United States Patent [19]

Laue et al.

[11] Patent Number: 4,858,063
[45] Date of Patent: Aug. 15, 1989

[54] SPIRAL CONFIGURATION OF ELECTRODES AND DIELECTRIC MATERIAL FOR SENSING AN ENVIRONMENTAL PROPERTY

[75] Inventors: Eric G. Laue, San Marino; James B. Stephens, La Crescenta, both of Calif.

[73] Assignee: California Institute of Technology, Pasadena, Calif.

[21] Appl. No.: 140,295

[22] Filed: Dec. 31, 1987

[51] Int. Cl.$^4$ .............................................. H01G 7/00
[52] U.S. Cl. .................................... 361/286; 73/336.5
[58] Field of Search ............... 427/79; 29/25.42; 73/336.5; 338/35, 34; 174/36, 115; 361/286

[56] References Cited
U.S. PATENT DOCUMENTS

| 336,773 | 2/1886 | Weil | 73/336.5 |
|---|---|---|---|
| 3,105,214 | 9/1963 | Blythe et al. | 73/336.5 X |
| 3,683,243 | 8/1972 | Rockliff | 361/286 |
| 4,083,765 | 4/1978 | Lawson | 204/195 |
| 4,140,990 | 2/1979 | Katz de Warren | 338/35 |
| 4,143,177 | 3/1979 | Kovac et al. | 427/79 |
| 4,549,134 | 10/1985 | Weiss | 338/34 |

Primary Examiner—Donald A. Griffin
Attorney, Agent, or Firm—Freilich Hornbaker Rosen & Fernandez

[57] ABSTRACT

A reliable moisture-indicating capacitive sensor is provided with wire electrodes at least one of which includes a coating of moisture-absorbing dielectric material by spirally twisting the wire electrodes about each other, thereby establishing a pair of electrodes in contact with opposite surfaces of a layer of dielectric material, and assuring consistent contact of each electrode with the dielectric material despite changes in environmental conditions.

4 Claims, 1 Drawing Sheet

SPIRAL CONFIGURATION OF ELECTRODES AND DIELECTRIC MATERIAL FOR SENSING AN ENVIRONMENTAL PROPERTY

ORIGIN OF INVENTION

The invention described herein was made in the performance of work under a NASA contract, and is subject to the provisions of Public Law 96-517 (35 USC 202) in which the Contractor was elected to retain title.

BACKGROUND OF THE INVENTION

This invention relates to a device for sensing a property in the environment, such as moisture, and more particularly to a new structure for such a device.

One type of device for sensing an environmental property includes a layer of dielectric material and a pair of plates in contact with opposite faces of the layer. A circuit or instrument connected to the electrodes enables changes in an electrical characteristic of the dielectric layer caused by a change in an environmental property to be sensed. For example, the capacitance measured between the electrodes may vary with environmental humidity if the dielectric material is one that absorbs moisture from the atmosphere. U.S. patent application Ser. No. 746,809 filed June 20, 1985, and now U.S. Pat. No. 4,662,220 issued May 5, 1987, describes a sensor of tyis type. In another example, variations in the resistivity of the material is measured to determine humidity. See U.S. Pat. No. 4,083,765.

One problem encountered in constructing either type of sensor is in assuring uniform surface contact between each electrode and a surface of the dielectric layer, especially in a simple construction designed to leave the dielectric layer well exposed to the environment, as in the aforesaid U.S. Pat. No. 4,083,765 which utilizes a Nafion tube to absorb moisture and two spiral wound coils as electrodes, one against the inside and the other against the outside of the Nafion tube. If a gap develops between one of the electrodes and the dielectric material due to changes in temperature, aging, etc., the gap will affect the output of the sensor. A simple construction of dielectric and electrodes which assures continual constant surface contact, especially while providing large area exposure of the dielectric to the environment, would be of considerable value.

SUMMARY OF THE INVENTION

In accordance with one embodiment of the present invention, a sensor is provided of the type wherein changes in an electrical property of a selected dielectric material are detected through a pair of electrodes coupled to opposite surfaces of the dielectric material, which assures constant contact of the electrodes with the dielectric material. The dielectric material has a pain of opposite surfaces and is sandwiched between a pair of electrodes. The electrodes are spirally twisted, one about the other, with the dielectric material between them. Elastic deformation of the parts due to their having been spirally twisted about one another assures that the electrodes will press tightly against the opposite surfaces of the dielectric material despite changes in environmental conditions that might otherwise cause gaps between the electrodes and the dielectric material, such as variation in temperature.

Each of the electrodes can be in the form of a wire, and the dielectric material in the form of a film that surrounds one or both of the wire electrodes. The wires are then spirally twisted about one another. One or more additional bare wires can be included in the spirally twisted bundle to enable monitoring of the transducer, such as during laboratory testing and calibration.

The novel features that are considered characteristic of this invention are set forth with particularity in the appended claims. The invention will best be understood from the following description when read in connection with the accompanying drawings.

DESCRIPTION OF THE PREFERRED EMBODIMENTS

Figure 1:
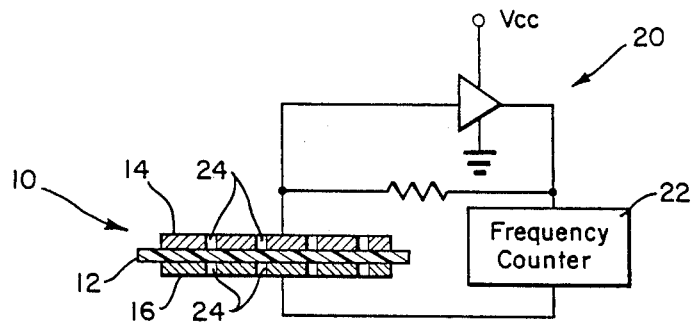
FIG. 1 is a schematic diagram of the prior art showing a sensor that operates on largely the same principles as that of the present invention, but having a previous construction, and showing it connected to a circuit that includes a frequency counter for measuring changes in the dielectric constant of the material between capacitor plates of the sensor.

FIG. 1 illustrates a transducer 10 of a configuration described in the the aforesaid U.S. Pat. No. 4,622,220, which can sense the relative humidity in the environment. The transducer includes a layer 12 of water-absorbing material and a pair of electrodes 14 and 16 in contact with opposite surfaces of the layer 12 that is formed, for example, of a polyphosphoric acid film or sulfonated fluorocarbon polyer, such as Nafion sold by DuPont Company, which absorbs moisture from the environment of the transducer, and whose dielectric constant varies with the amount of moisture absorbed. The transducer 10 serves as the capacitive element of an RC oscillator circuit 20 the frequency of which depends upon the capacitance of the transducer 10, and therefore on the moisture absorbed from the environment. A frequency counter 22 measures the frequency of the oscillator to indicate the humidity in the atmosphere. Each of the electrodes 14 and 16 is porous, as indicated by the holes 24, to facilitate the absorption and desorption of moisture in the layer 12 from the environment.

Figure 2:
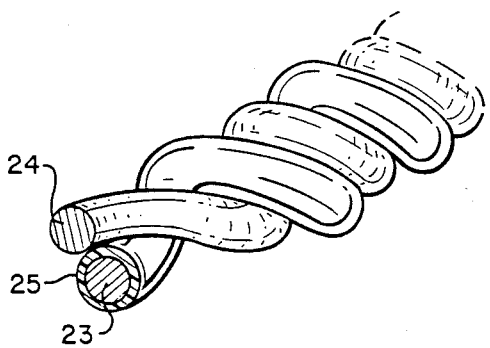
FIG. 2 is a partial perspective view of a sensor constructed in accordance with one embodiment of the present invention.

FIG. 2 illustrates a first embodiment of the invention consisting of two wires 23 and 24, with the first wire 23 coated with a layer 25 of dielectric material. The wires are spirally twisted about one another to form a tightly wound pair of spiraled wires. Each of the wires undergoes such elastic deformation that is presses toward the other as it tends to return to its initial state after deformation. In that manner, the wires remain in firm contact with the dielectric material despite aging or changes in the environment, such as changes in temperature, and consequent differential expansion or contraction of the contacts which might open small gaps between the wires and the dielectric material. Instead, such changing factors cause only slight increase or decrease of the elastic deformation of the twisted wires without totally eliminating the elasticity that urges the axes of the wires toward each other. By providing the dielectric material in the form of a layer surrounding one wire, it will always be present in the direct line between opposite points along the axes of the wires.

An alternative to the embodiment of FIG. 2 is the provision of a layer of dielectric material on both wires. That has the advantage of symmetry between the wires so that upon spirally twisting them together, each undergoes substantially the same elastic deformation. Yet another alternative is to provide two wires coated with layers of dielectric material, and one or preferably two bar wires to retain symmetry in the twisting of the wires, as will be described with reference to FIGS. 3, 4 and 5. The bare wires can be paired with the coated wires to provide two sensors subject to the same environmental conditions. Alternatively, the bare wires may be used to monitor the one sensor, comprised of two spirally twisted coated wires.

It is difficult to maintain the electrodes 14, 16 in unchanging contact with the surfaces of the moisture-absorbing layer because changes, such as the temperature of the environment and aging, can cause warping of the electrodes and dielectric layer that can cause one part to move out of contact with another. If a gap opens between a surface of the layer 12 and one of the electrodes, the measured capacitance will be affected, which can be confused with a change in absorbed moisture. Maintaining a steady contact can be especially difficult where the electrodes are made porous to facilitate the interchange of moisture between the moisture-absorbing layer 12 and the atmosphere.

Figure 3:
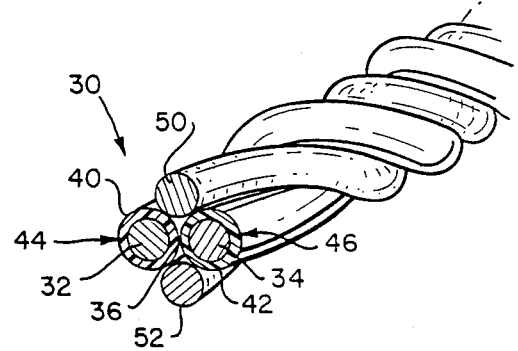
FIG. 3 is a partial perspective view of a sensor constructed in accordance with a second embodiment of the present invention.

Referring now to FIG. 3, it illustrates a sensor 30 of the present invention which assures virtually unchanging contact between a pair of wire electrodes 32 and 34, each coated with a separate layer of dielectric material 36. Such constant contact is assured basically by twisting the coated wire electrodes 32 and 34 about one another to form tightly wound spirals. During such twisting, each of the wire electrodes undergoes elastic deformation which urges it to press toward the other wire electrode.

Figure 4:
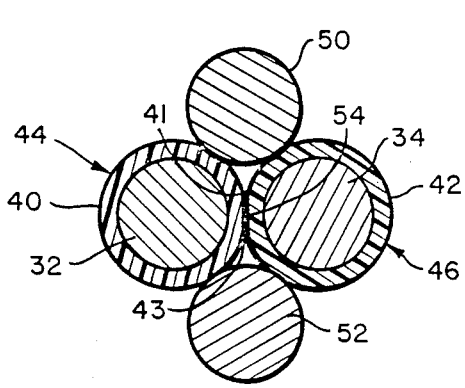
FIG. 4 is a sectional view of the sensor of FIG. 3.
Figure 5:
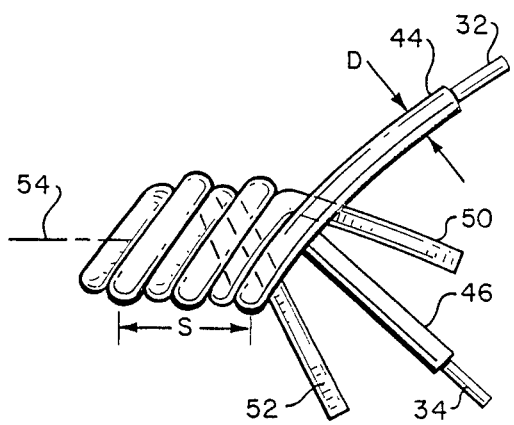
FIG. 5 is a plan view of an end portion of the sensor of FIG. 3.

In the transducer of FIGS. 3-5, the dielectric material 36 includes two cylindrical layers 40 and 42 that are each moisture absorbing and whose dielectric constant depends upon its moisture content. Each electrode 32 and 34 is thus in the form of a wire, and each cylindrical layer 40 and 42 fully surrounds a corresponding wire. Each combination 44 and 46 of a wire electrode and surrounding dielectric material is tightly twisted, one about the other, to introduce elastic deformation in the combinations that will urge them tightly together. As shown in FIG. 3, only a limited region between points 41 and 43 of the dielectric material 36 formed by the two layers 40 and 42 are in direct contact, and only this limited region has a significant effect on the measured capacitance between the two wire electrodes 32 and 34. However, the major determinant of the accuracy of the transducer is the constancy of the area of contact of the wire electrodes with the limited region of the dielectric layer 36, rather than the total capacitance between the wire electrodes of the transducer.

Although a transducer with only the two combinations 44 and 46 of dielectric material surrounding two wires, and with the combinations spirally twisted tightly about one another, is sufficient, it is preferable to also include one or two bare wires 50 and 52 in the spiral structure of the sensor, primarily to facilitate and maintain symmetrical twisting of the wire electrodes 32 and 34. However, as noted above, each bare wire, such as 50, enables a separate measurement to be made of characteristics of the sensor, as by providing an additional measurement of the dielectric constant of the material at a different location between the bare wire and one of the coated wire electrodes, such as electrodes 32, with a different portion of the dielectric film 40 being active between them. This has the advantage of enabling measurements of the dielectric material by changes in its resistance. This might be done during laboratory testing and calibration when effects of the measuring current, such as generated heat, can be taken into account.

A structural advantage of using two bare wires 50 and 52 to make the spiral wound sensor symmetrical about an imaginary line connecting the two wire electrodes 32 and 34. And it is preferable to make the pitch of the spiral transducer (the spacing S between adjacent turns of wire electrode) be less than ten times the diameter D of a combination of wire and surrounding dielectric material in order to provide significant elastic deformation.

There are a variety of ways of ending the spiral wound sensor. One way is shown in FIG. 5 wherein each of the electrode combinations 44 and 46 and of the bare wires 50 and 52 in led off at a different angle from the axis 54 of the spiral wound sensor. Of course, connections need only be made at one end of the sensor, since current flow is between the electrodes through the dielectric material of the sensor rather than through the lengths of the wire electrodes. However, the connections can be made to the wire electrodes at opposite ends of the spirally wound sensor.

Thus, the invention provides a sensor of the type which includes a pair of spirally twisted wire electrodes against opposite surfaces of dielectric material. That assures constant contact of the electrodes with the surfaces of the dielectric material. This is accomplished by spirally twisting the electrodes about one another. The dielectric material is maintained between them, preferably by coating one or both twisted wires with the dielectric material. The transducer may include one or more additional wires in contact with the dielectric films to facilitate monitoring of the transducer, such as during laboratory testing and calibration.

In practice, it has been found that about two hours are required for a moisture sensor configured in this spiral manner to reach a stable level when introduced from a dry storage area to a humid area, but that once it reaches a stable level, if follows changes in humidity very faithfully without anomalies otherwise produced by loss of contact (separations) between the electrodes and the dielectric material due to changes in the environment. The sensor is therefore useful for continuous monitoring of humidity in an environment that is subject to changes in the environment such as changes in temperature. The concept of the invention may be readily adapted to sensors for other environmental properties by simply making a judicious choice of the dielectric material. The advantages of the humidity sensor would still be present in the different property sensor.

Although particular embodiments of the invention have been described and illustrated herein, it is recognized that modifications and variations may readily occur to those skilled in the art, such as the manner in which the dielectric material is provided to surround at least one of the electrodes, or the nature of the dielectric material which may be selected to detect the presence and level of a wide variety of gas samples, such as those enumerated in the prior U.S. Pat. No. 4,083,765. What is important is that the electrodes be elongated and tightly twisted to form multiturn spiraled electrodes, each tightly engaging the dielectric material between them. The elastic deformation produced in each will tend to urge the electrodes against the opposite sides of the dielectric material. That is distinct from the coils of the prior U.S. Pat. No. 4,083,765 which may tend to expand and contract in diameter due to changes in the environmental conditions, such as temperature. Consequently, it is intended that the claims be interpreted to cover such modifications and variations.

What is claimed is:

1. A spiral sensor comprising
   first and second elongated electrodes, and
   a layer of dielectric material surrounding each of said elongated electrodes separately, said dielectric material having electrical properties that vary with a characteristic of the environment, and
   at least one bare wire,
   said elongated electrodes separately surrounded by dielectric material being spirally twisted, each one about the other, to form a pair of multiturn electrodes spiraled with said bare wire, each elongated electrode tightly engaging said dielectric material, said dielectric material being distributed throughout the length of said spiral sensor, whereby said electrodes and dielectric material surrounding each electrode are urged into constant contact with each other and said bare wire.

2. A sensor comprising first and second elongated electrodes, each of said electrodes being in the form of a wire, a layer of dielectric material provided as a separate film surrounding each of said wire electrodes, said dielectric material having electrical properties that vary with a characteristic of the environment, and including at least one bare wire, said wire electrodes and said bare wire being spirally twisted together about each other to form a pair of multiturn spiraled electrodes, each tightly engaging said dielectric material, said dielectric material being distributed throughout the length of said spiral sensor, whereby said wire electrodes with surrounding dielectric material are urged into constant contact.

3. A sensor comprising first and second elongated electrodes, each of said electrodes being in the form of a wire, a layer of dielectric material provided as a separate film surrounding each of said wire electrodes, said dielectric material having electrical properties that vary with a characteristic of the environment, and including a pair of bare wires, said wire electrodes and bare wires being spirally twisted together about each other with said bare wires separated from each other by wire electrodes having a surrounding film of dielectric material to form a pair of multiturn spiraled electrodes, each tightly engaging said dielectric material, said dielectric material being distributed throughout the length of said spiral sensor, whereby said wire electrodes with surrounding dielectric material are urged into constant contact.

4. A sensor comprising
   a pair of electrically conductive wires,
   a film of moisture absorbing dielectric material whose dielectric coefficient varies as a function of moisture absorbed, said film being disposed about each of said wires to form two film-enclosed wire electrodes,
   said two film-enclosed wire electrodes being spirally twisted about each other to elastically deform said wire electrodes into a pair of tightly engaged multiturn spirals, and
   including at least one bare wire twisted together with said wire electrodes, said bare wire being in contact with the dielectric film of both of said wire electrodes throughout the length of said multiturn spirals.

* * * * *